US011002715B2

(12) United States Patent
Hioki

(10) Patent No.: US 11,002,715 B2
(45) Date of Patent: May 11, 2021

(54) METHOD FOR LIQUID CHROMATOGRAPHIC MASS SPECTROMETRY AND LIQUID CHROMATOGRAPH MASS SPECTROMETER

(71) Applicant: SHIMADZU CORPORATION, Kyoto (JP)

(72) Inventor: Yusaku Hioki, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 228 days.

(21) Appl. No.: 15/973,640

(22) Filed: May 8, 2018

(65) Prior Publication Data
US 2018/0328898 A1 Nov. 15, 2018

(30) Foreign Application Priority Data
May 11, 2017 (JP) .............................. JP2017-094873

(51) Int. Cl.
G01N 30/38 (2006.01)
G01N 30/84 (2006.01)
(Continued)

(52) U.S. Cl.
CPC .............. *G01N 30/38* (2013.01); *G01N 30/28* (2013.01); *G01N 30/7233* (2013.01);
(Continued)

(58) Field of Classification Search
CPC .... G01N 30/38; G01N 30/28; G01N 30/7233; G01N 30/84; G01N 33/6848;
(Continued)

(56) References Cited

U.S. PATENT DOCUMENTS

2014/0099725 A1* 4/2014 Williams ........... G01N 33/6848
436/87
2014/0315318 A1* 10/2014 Lu ........................ G01N 33/15
436/93
2017/0315101 A1* 11/2017 Green .................. G01N 30/724

FOREIGN PATENT DOCUMENTS

GB 2535269 A 8/2016
JP 9-229920 A 9/1997
(Continued)

OTHER PUBLICATIONS

Lexico.com Definition of Program (Retrieved Apr. 2020) (Year: 2020).*

(Continued)

*Primary Examiner* — Benjamin R Whatley
*Assistant Examiner* — Jean Caraballo-Leon
(74) *Attorney, Agent, or Firm* — Sughrue Mion, PLLC

(57) ABSTRACT

In an LC/MS analysis of a sample containing various compounds, additive supply pumps 164A and 164B in a post-column adding unit 16 draw and supply different kinds of additives A and B from containers 163A and 163B, respectively. The additives are mixed into an eluate through T-joints 162 and 161. A preferable combination of the additives is the combination of DMSO which produces the effect of gathering charge states and 2-propanol which produces the effect of promoting atomization or vaporization of droplets. By mixing the two additives into the eluate while mixing them at an appropriate flow-rate ratio according to a previously determined flow-rate program, the ionization efficiency can be nearly optimized for each compound during the process of generating ions by spraying electrically charged droplets of the eluate from an ESI spray 21. Consequently, the detection sensitivity becomes higher than conventional levels.

8 Claims, 3 Drawing Sheets

(51) Int. Cl.
    *G01N 30/72*   (2006.01)
    *G01N 30/28*   (2006.01)
    *H01J 49/16*   (2006.01)
    *G01N 33/68*   (2006.01)
    *H01J 49/04*   (2006.01)
    *G01N 30/02*   (2006.01)

(52) U.S. Cl.
    CPC ......... *G01N 30/84* (2013.01); *G01N 33/6848* (2013.01); *H01J 49/0431* (2013.01); *H01J 49/16* (2013.01); *H01J 49/165* (2013.01); *G01N 2030/027* (2013.01)

(58) Field of Classification Search
    CPC .............. G01N 2030/027; G01N 30/02; H01J 49/0431; H01J 49/16; H01J 49/165
    See application file for complete search history.

(56) References Cited

FOREIGN PATENT DOCUMENTS

| | | |
|---|---|---|
| JP | 2004-125453 A | 4/2004 |
| WO | 2016/082044 A1 | 6/2016 |

OTHER PUBLICATIONS

Stephenson et al (Simplification of Product Ion Spectra Derived from Multiply Charged Parent Ions via Ion/Ion Chemistry, Anal. Chem. 1998, 70, 17, 3533-3544) (Year: 1998).*

Pan et al (Nanoelectrospray Ionization of Protein Mixtures: Solution pH and Protein pI, Anal. Chem. 2004, 76, 4, 1165-1174) (Year: 2004).*

Zaia et al (Mass Spectrometry and Glycomics, Journal of Integrative Biology, 2010, 14, 4, pp. 401-418) (Year: 2010).*

Liigand et al (pH Effects on Electrospray Ionization Efficiency, Journal of the American Society for Mass Spectrometry, 2016, 28, pp. 461-469) (Year: 2016).*

Zhou et al (Protonation in Electrospray Mass Spectrometry: Wrong-Wat-Round or Right-Way-Round?, American Society for Mass Spectrometry, 2000, 11, pp. 961-966) (Year: 2000).*

"LC-MS No Hanashi, Sono 4: Bunri Oyobi Ionka Ni Juuyouna Idousou (LC-MS Talk, Part 4: Important Mobile Phase for Separation and Ionization)", Shimadzu Corporation, [online], [accessed on Apr. 17, 2017], the Internet, <URL: http://www.an.shimadzu.co.jp/hplc/support/lib/lctalk/57/57intro.htm>, pp. 1-3.

Anthony T. Iavarone, et al., "Supercharged Protein and Peptide Ions Formed by Electrospray Ionization", Analytical Chemistry., 2001, pp. 1455-1460, vol. 73, No. 7.

Hannes Hahne, et al., "DMSO enhances electrospray response, boosting sensitivity of proteomic experiments", Nature Methods, Oct. 2013, pp. 989-991, vol. 10, No. 10.

Communication dated Sep. 10, 2018 from the European Patent Office in counterpart application No. 18170686.2.

Communication dated Jun. 23, 2020 from the Japanese Patent Office in counterpart application No. 2017-094873.

Communication dated Feb. 9, 2021 from the Japanese Patent Office in Application No. 2017-094873.

* cited by examiner

METHOD FOR LIQUID CHROMATOGRAPHIC MASS SPECTROMETRY AND LIQUID CHROMATOGRAPH MASS SPECTROMETER

TECHNICAL FIELD

The present invention relates to an analyzing method using a liquid chromatograph mass spectrometer employing a mass spectrometer as a detector for a liquid chromatograph, as well as a liquid chromatograph mass spectrometer suitable for the same analyzing method.

BACKGROUND ART

In a liquid chromatograph mass spectrometer (which may be hereinafter abbreviated as the "LC-MS"), a so-called "atmospheric pressure ionization (API) method", such as an electrospray ionization (ESI) method, atmospheric pressure chemical ionization (APCI) method or atmospheric pressure photoionization (APPI) method, is employed to ionize compounds in an eluate supplied from a column of a liquid chromatograph. In an atmospheric pressure ion source employing an atmospheric pressure ionization method, the eluate is sprayed through a spray nozzle into an ambience of substantially atmospheric pressure, and the compounds in the fine droplets produced by the spraying process are ionized to generate gaseous ions. Therefore, in order to improve the ionization efficiency, it is important to promote atomization and vaporization of the sprayed droplets.

The largest portion of the eluate introduced into the atmospheric pressure ion source is the mobile phase used in the liquid chromatograph. If the mobile phase is simply composed of water, alcohol, acetonitrile (ACN) or other basic substances, the characteristics of the mobile phase may not be suitable for performing satisfactory ionization in an atmospheric pressure ion source. Accordingly, for an LC-MS, an appropriate kind of reagent is often used as an additive to the mobile phase according to the characteristics of the sample, kind of mobile phase used, kind of ionization method and other related factors in order to improve the ionization efficiency (for example, see Non Patent Literature 1). Normally, such an additive is often mixed into the mobile phase. For an additive which may affect the separation characteristics of the column in the liquid chromatograph, the so-called "post-column" method is used, in which the reagent is mixed into the eluate exiting from the outlet of the column instead of being mixed into the mobile phase before the mobile phase is introduced into the column (for example, see Patent Literature 1).

In the case of adding a reagent by the post-column method, the compounds in the sample have already been separated at the point of the addition of the reagent. Accordingly, it is essential to appropriately determine not only the kind and amount of reagent to be added, but also the timing of the addition according to the compound, because the effectiveness of the reagent varies depending on the characteristics and concentration of the compound even when the same reagent is used. Besides, in the case of a gradient analysis, since the mixture ratio of the mobile phases changes with time, the effectiveness of the reagent may change with the mixture ratio even when the same reagent is used. Furthermore, in the case of the post-column method, an increase in the amount of addition of the reagent directly increases the amount of eluate introduced into the atmospheric pressure ion source. Therefore, for example, adding a highly volatile reagent in greater quantity does not always enhance the ionization efficiency.

However, in the case of performing a measurement on a sample containing various compounds with different characteristics, it is difficult to set the addition condition of the reagent so that a high level of ionization efficiency can be achieved for each of those various compounds. Accordingly, in conventional LC-MSs, the addition condition of the reagent is not always optimized for all various compounds to achieve the highest or nearly highest level of ionization efficiency. In some cases, the detection sensitivity in the mass spectrometer is sacrificed.

CITATION LIST

Patent Literature

Patent Literature 1: JP 2004-125453 A (Paragraph [0021])

Non Patent Literature

Non Patent Literature 1: "LC-MS No Hanashi, Sono 4: Bunri Oyobi Ionka Ni Juuvouna Idousou (LC-MS Talk, Part 4: Important Mobile Phase for Separation and Ionization)", Shimadzu Corporation, [online], [accessed on Apr. 17, 2017], the Internet Non Patent Literature 2: Anthony T. Iavarone and two other authors, "Supercharged Protein and Peptide Ions Formed by Electrospray Ionization", *Anal. Chem.*, 2001, Vol. 73, pp. 1455-1460

Non Patent Literature 3: Hannes Hahne and nine other authors, "DMSO enhances electrospray response, boosting sensitivity of proteomic experiments", *Nature Methods*, October 2013, Vol. 10, No. 10, pp. 989-991

SUMMARY OF INVENTION

Technical Problem

The present invention has been developed to solve the previously described problem. Its objective is to provide a method for liquid chromatographic mass spectrometry and a liquid chromatograph mass spectrometer in which the ionization efficiency in an atmospheric pressure ion source is improved for various compounds contained in a sample so that a higher detection sensitivity can be achieved as compared to conventional techniques.

Solution to Problem

The method for liquid chromatographic mass spectrometry according to the present invention developed for solving the previously described problem is an analyzing method in which a liquid chromatograph mass spectrometer employing a mass spectrometer including an atmospheric pressure ion source is used as a detector for a liquid chromatograph. In the method:

at least two kinds of additives as a first additive and a second additive are mixed into an eluate flowing in a passage connecting an outlet of a column of the liquid chromatograph and the atmospheric pressure ion source, where each of the two additives is mixed into the eluate at an arbitrary flow rate; and the first additive is a reagent which affects the charge state of the eluate, while the second additive is a reagent which affects the size of droplets of the eluate or vaporization efficiency of the droplets when the eluate is sprayed into an ambience of atmospheric pressure in the atmospheric pressure ion source.

The liquid chromatograph mass spectrometer according to the present invention developed for solving the previously described problem is a device suitable for carrying out the method for liquid chromatographic mass spectrometry according to the present invention. In a liquid chromatograph mass spectrometer in which a mass spectrometer provided with an atmospheric pressure ion source is used as a detector for a liquid chromatograph, the present device includes:

a) an additive supplier for mixing an additive into an eluate flowing in a passage connecting an outlet of a column of the liquid chromatograph and the atmospheric pressure ion source, the additive supplier including at least a first additive supply section for mixing a first additive at a given flow rate into the eluate and a second additive supply section for mixing a second additive at a given flow rate into the eluate; and b) a controller for controlling the flow rate of the first additive supplied by the first additive supply section and the flow rate of the second additive supplied by the second additive supply section, the flow rates adjusted independently of each other.

In the liquid chromatograph mass spectrometer according to the present invention, each of the first and second additive supply sections may include: an additive container for holding an additive in a liquid form; a liquid supply pump for drawing the additive from the additive container and supplying the additive at a predetermined flow rate; and a passage for merging the additive supplied from the liquid supply pump into the eluate transported from the outlet of the column to the atmospheric pressure ion source. The plurality of additives supplied from the liquid supply pumps may be mixed together before being merged into the eluate, or each additive may be individually merged into the eluate. The additive supplier may further include another additive supply section in addition to the first and second additive supply sections. That is to say, the device may be configured to be capable of mixing three or more kinds of additives into the eluate.

In the liquid chromatograph mass spectrometer according to the present invention, the first additive supply section adds the first additive to the eluate at an appropriate flow rate, while the second additive supply section adds the second additive to the eluate at an appropriate flow rate, under the control of the controller. Accordingly, an eluate in which the first and second additives have been mixed reaches the atmospheric pressure ion source. In the atmospheric pressure ion source, the eluate is sprayed into an ambience of atmospheric pressure. Through this spraying process, the eluate is atomized into droplets, and the compounds (sample components) in those droplets are ionized.

The ionization mechanism itself depends on the technique used for the atmospheric pressure ionization, such as the ESI, APCI or APPI. In any case, the ionization efficiency mainly depends on the conditions concerning the electric charging, such as the ease of charging of the eluate introduced into the atmospheric pressure ion source, as well as the conditions concerning the ease of ejection of the compound (or ion) in a gasified form, such as the size of the droplets sprayed into the ambience of substantially atmospheric pressure and the ease of vaporization of the solvent in those droplets. Accordingly, in the method for liquid chromatographic mass spectrometry according to the present invention, a reagent which affects the charge state of the eluate is used as the first additive, while a reagent which affects the size of the droplets of the eluate or vaporization efficiency of the droplets when the eluate is sprayed into the ambience of atmospheric pressure in the atmospheric pressure ion source is used as the second additive. The flow rates at which the two kinds of additives, i.e. the first and second additives, are respectively mixed are appropriately adjusted according to the kind and characteristics of the compound contained in the sample, the kind of mobile phase and other factors. The appropriate amounts of addition of the two additives can be experimentally investigated.

By mixing the two or more kinds of additives with different characteristics into the eluate by the post-column method and introducing them into the atmospheric pressure ion source, the ionization efficiency in the atmospheric pressure ion source for various compounds can be improved to be higher than conventional levels. Accordingly, a larger quantity of ions can be subjected to mass spectrometry for any of the compounds, and the detection sensitivity can be thereby improved. Therefore, for example, it will be possible to detect a compound which cannot be detected by conventional techniques. Furthermore, a mass spectrum with a sufficient level of signal intensity can be obtained for a compound for which a sufficient signal intensity for qualitative determination or structural analysis has not been conventionally obtained, so that the qualitative determination or structural analysis can be accurately performed.

In the liquid chromatograph mass spectrometer according to the present invention, the controller may preferably be configured to control an operation of the first additive supply section and the second additive supply section according to a program in which the flow rate of the first additive and the flow rate of the second additive can be individually changed according to the passage of time.

According to this configuration, the program can be appropriately set beforehand so as to mix two or more kinds of additives into the eluate in such a manner that their respective amounts of addition continuously change with time. Consequently, each target compound can be assuredly detected with a high level of sensitivity.

In the method for liquid chromatographic mass spectrometry according to the present invention, typically, the first additive is a reagent for pH control and/or having a high level of proton affinity, and the second additive is a reagent having at least one nature selected from a lower boiling point, a lower surface tension and a lower viscosity than a mobile phase.

There are various kinds of reagents available as the first or second additive. Aqueous ammonia, triethylamine, acetic acid, formic acid, trifluoroacetic acid, ammonium acetate, and ammonium formate, which are all commonly used pH-control reagents, can be used as the first additive, i.e. the reagent which affects the charge state of the eluate. Dimethyl sulfoxide (DMSO), m-nitrobenzyl alcohol (m-NBA, where m is 2, 3 or 4) and glycerol may also be used as the first additive. These reagents affect the charge state distribution of the ions. It is known that DMSO has a charge-state-gathering effect, while m-NBA and glycerol have a charge-state-increasing effect (see Non Patent Literature 2). On the other hand, acetonitrile, 2-propanol, methanol, ethanol, 1-propanol, acetone and other organic solvents can be used as the second additive, i.e. the reagent having a lower boiling point, lower surface tension or lower viscosity than the mobile phase.

A study by the present inventor suggested that it is preferable to use DMSO as the first additive and 2-propanol as the second additive, both of which are easily available and highly effective. DMSO is a polar aprotic solvent. It produces the effect of gathering charge states and is therefore effective for ionizing a compound. However, DMSO has a high boiling point and is difficult to be vaporized. On the other hand, 2-propanol has a low boiling point and is easy to be vaporized. It also has a low surface tension, which helps the formation of fine droplets. Thus, 2-propanol can compensate for the shortcomings of DMSO in terms of the generation of gaseous ions in the atmospheric pressure ion source. The use of such additives can particularly improve the detection sensitivity for high-molecular compounds of biological origin, such as peptides or sugar chains.

In one possible mode of the method for liquid chromatographic mass spectrometry according to the present invention, the sample to be subjected to a measurement is a mixture of a peptide and a glycopeptide, the first additive is a pH-control reagent, and the flow rate of the first additive is changed with the passage of time in such a manner that the eluate exiting from the outlet of the column of the liquid chromatograph becomes acidic during a period of time in which the peptide is contained in the eluate, whereas the eluate exiting from the outlet of the column of the liquid chromatograph becomes basic during a period of time in which the glycopeptide is contained in the eluate.

In this case, the polarity of the ion to be detected may be switched so as to perform a positive ion measurement in the mass spectrometer during a period of time in which a peptide and a glycopeptide including a neutral sugar chain are eluted, and to perform a negative ion measurement in the mass spectrometer during a period of time in which a glycopeptide including an acidic sugar chain is eluted. By this operation, a high level of sensitivity can be achieved in detecting any of the three kinds of substances contained in the sample, i.e. a peptide, a glycopeptide including a neutral sugar chain, and a glycopeptide including an acidic sugar chain.

As noted earlier, there are various ionization methods adoptable in the atmospheric pressure ion source of the liquid chromatograph mass spectrometer used in the method for liquid chromatographic mass spectrometry according to the present invention. The present invention is particularly suitable in the case where an electrospray ion source is used as the atmospheric pressure ion source.

An electrospray ion source sprays an eluate into an ambience of substantially atmospheric pressure while electrically charging the droplets by the effect of a high electric field. The compounds, such as peptides, are ionized through the atomization process which includes the splitting of the charged droplets into finer particles. DMSO and some other reagents have a lower surface tension than water and therefore more easily allows the atomization of the droplets. The atomization of the charged droplets facilitates the Coulomb repulsive force to act inside each droplet as well as promotes the ejection of gaseous ions, whereby the ionization efficiency is improved (see Non Patent Literature 3). That is to say, when the method for liquid chromatographic mass spectrometry: according to the present invention is applied in a liquid chromatograph mass spectrometer employing an electrospray ion source, the effect of gathering charge states and the effect of promoting the atomization of the droplets by the additives are combined together, so that the ionization efficiency can be more noticeably improved.

Advantageous Effects of the Invention

With the liquid chromatograph mass spectrometer and the method for liquid chromatographic mass spectrometry according to the present invention, the ionization efficiency in an atmospheric pressure ion source can be improved to the highest or nearly highest level for each of the various compounds contained in a sample. Therefore, a higher level of detection sensitivity can be achieved than in the case of a conventional analyzing method or device.

DESCRIPTION OF EMBODIMENTS

One embodiment of the LC-MS according to the present invention, and one embodiment of an analyzing method using the LC-MS, are hereinafter described with reference to the attached drawings.

Figure 1:
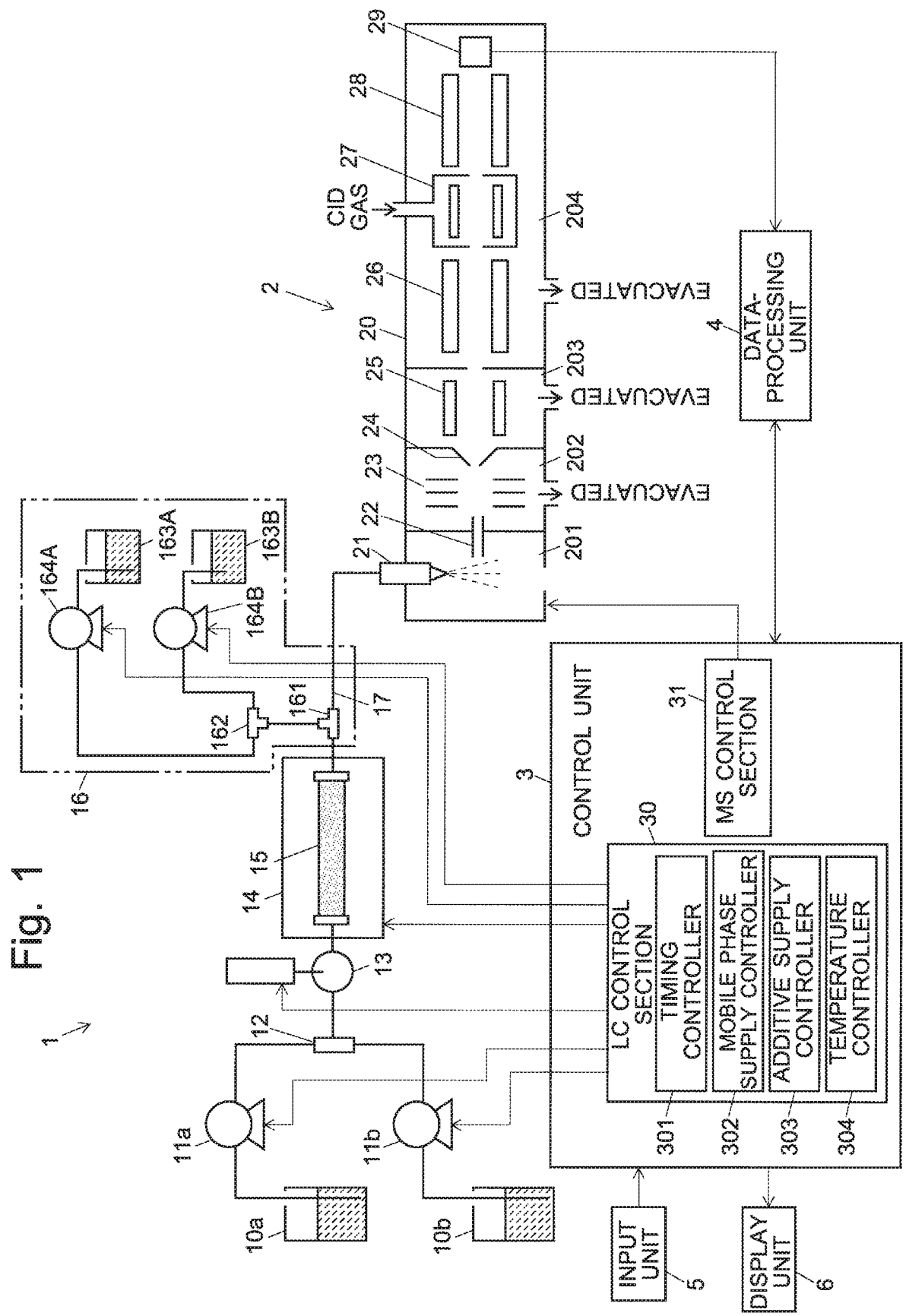
FIG. 1 is an overall configuration diagram of an LC-MS as one embodiment of the present invention.

FIG. 1 is an overall configuration diagram of the LC-MS in the present embodiment.

The LC-MS in the present embodiment includes a liquid chromatograph unit (LC unit) 1, mass spectrometer unit (MS unit) 2, control unit 3, data-processing unit 4, as well as an input unit 5 and display unit 6 which serve as user interfaces.

The LC unit 1 includes: liquid supply pumps 11a and 11b for drawing mobile phases a and b from two mobile phase containers 10a and 10, respectively, and for supplying those mobile phases; a mixer 12 for mixing the two mobile phases a and b; an injector 13 for injecting a liquid sample into a mobile phase; a column 15 for separating compounds; a column oven 14 for controlling the temperature of the column 15; and a post-column adding unit 16 provided in an eluate passage 17 on the outlet side of the column 15. The post-column adding unit 16 includes: a first T-joint 161 located on the eluate passage 17; a second T-joint 162 connected to the first T-joint 161; two additive containers 163A and 163B which respectively contain different kinds of additives A and B; and two additive supply pumps 164A and 164B for drawing additives A and B from the additive containers 163A and 163B, respectively, and for supplying those additives.

The MS unit 2 has a chamber 20, which is partitioned into an ionization chamber, first intermediate vacuum chamber 202, second intermediate vacuum chamber 203 and a high vacuum chamber 204. The inside of the ionization chamber 201 is maintained at substantially atmospheric pressure, while the high vacuum chamber 204 is maintained in a high vacuum state by a high-performance vacuum pump (not shown). The first and second intermediate vacuum chambers 202 and 203 are individually evacuated by vacuum pumps so that the degree of vacuum creases in a stepwise manner from the ionization chamber 201 to the high vacuum chamber 204. An ESI spray 21 for performing ionization by the ESI method is provided within the ionization chamber 201. The ionization chamber 201 communicates with the first intermediate vacuum chamber 202 through a thin desolvation tube 22. The first intermediate vacuum chamber 202 contains an ion guide 23 for transporting ions while converging them. The first intermediate vacuum chamber 202 communicates with the second intermediate vacuum chamber 203 through an orifice formed at the apex of a skimmer 24. The second intermediate vacuum chamber 203 contains an ion guide 25 for transporting ions while converging them. The high vacuum chamber 204 contains a first quadrupole mass filter 26 and a second quadrupole mass filter 28 placed before and after a collision cell 27, respectively, with a detector 29 located behind the second mass filter. Detection signals obtained with the detector 29 are fed to the data-processing unit 4.

The control unit 3 includes an LC control section 30 for controlling the operation of each section of the LC unit 1, and an MS control section 31 for controlling the operation of each section of the MS unit 2. The LC control section 30 includes a timing controller 301, mobile phase supply controller 302, additive supply controller 303 and temperature controller 304.

A typical operation of the LC-MS in the present embodiment is as follows: The mobile phase supply controller 302 in the LC control section 30 controls the liquid supply pumps 11a and 11b to draw mobile phases a and b from the mobile phase containers 10a and 10b, respectively, and supply them at their respective flow rates, according to a previously determined program (time sequence) in which the relationship between the flow rate (or flow velocity) and the passage of time is specified. The two supplied mobile phases a and b are mixed together by the mixer 12 and sent through the injector 13 into the column 15. According to an instruction from the timing controller 301, a liquid sample is injected from the injector 13 into the mobile phase at a predetermined timing. The injected liquid sample is pushed by the mobile phase and sent into the column 15. While passing through the column 15, the various compounds in the liquid sample are separated from each other in the longitudinal direction of the column 15 (i.e. in the temporal direction), to be eluted from the outlet of the column 15 with different amounts of time lag. The temperature controller 304 regulates the temperature of the column oven 14 according to a previously determined temperature program, e.g. to maintain a constant temperature of 40° C.

Additive A which has an appropriate nature is previously prepared in the additive container 163A. Another additive B, which is a different kind from additive A and has an appropriate nature, is also previously prepared in the additive container 163B. The additive supply controller 303 controls each of the additive supply pumps 164A and 164B to draw and supply additives A and B prepared in the additive containers 163A and 163B, respectively, according to a previously determined additive supply program (time sequence). Being mixed together through the two T-joints 162 and 161, the two additives A and B are mixed into the eluate flowing through the eluate passage 17. That is to say, while the eluate containing the compounds separated by the column 15 is flowing through the post-column adding unit 16, the two additives A and B are mixed into the eluate in their respective appropriate quantities.

The eluate which has flown through the eluate passage 17 and reached the ESI spray 21 in the MS unit 2 is sprayed from the nozzle of the same spray 21 into an ambience of substantially atmospheric pressure while being ionized under the effect of a biased electric field created around the tip of the nozzle. Thus, fine charged droplets containing the compounds and solvent (including the mobile phase, solvent of the original liquid sample, and additives) are sprayed. Since a considerable amount of residual gas is present within the ionization chamber 201, the charged droplets released from the ESI spray 21 come in contact with the molecules of the residual gas and are thereby gradually divided into smaller particles. Meanwhile, the ionization chamber 201 is heated with a heater (not shown), whereby the vaporization of the solvent in the charged droplets is prompted. The compounds in the droplets capture electric charges and are ejected from the droplets to turn into gaseous ions. The generated ions are drawn into the desolvation tube 22 by the stream of gas formed by the pressure difference between the two ends of the desolvation tube 22, to be carried into the first intermediate vacuum chamber 202. Under the effect of the electric fields created by the ion guides 23 and 25, those ions are sequentially transported to the high vacuum chamber 204, where only an ion having a predetermined mass-to-charge ratio is selected as the precursor ion in the first quadrupole mass filter 26.

In the collision cell 27, a predetermined kind of collision gas, such as argon, is introduced. The ion which has passed through the first quadrupole mass filter 26 enters the collision cell 27 and is fragmented due to the collision induced dissociation. The various kinds of product ions generated by the fragmentation are introduced into the second quadrupole mass filter 28, where only a product ion having a specific mass-to-charge ratio is selected. Thus, the specific product ion which has originated from the specific precursor ion and passed through the second quadrupole mass filter 28 reaches the detector 29. The detector 29 produces a detection signal corresponding to the amount of incident ion. This signal is digitized in the data-processing unit 4 and then subjected to a predetermined data-processing operation. For example, a mass chromatogram is created based on the data sequentially obtained with the passage of time. An area value of a peak corresponding to the target compound on that mass chromatogramis calculated, and a quantitative value is calculated based on the area value.

The gradient program which determines the mixture ratio of the two mobile phases a and h in the LC/MS analysis, the program which determines the flow rate for each of the two additives A and B, as well as the temperature program for controlling the temperature of the column 14, should be previously set as part of the analysis conditions by an operator from the input unit 5.

In the LC-MS according to the present embodiment, two kinds of additives (reagents) A and B can be added to the eluate in the post-column adding unit 16. These additives do not affect separation characteristics in the LC unit 1. Therefore, it is preferable to determine the kinds of additives and the flow-rate program according to the kind of sample (kinds of compounds) to be subjected to the measurement, kinds of mobile phases and other factors so that the highest possible level of ionization efficiency will be achieved in the ESI spray 21, or the ESI ion source, in the MS unit 2. The combination of the two additives may be appropriately determined. In the case of the ESI ion source, the major factors which affect the ionization efficiency are the charge state immediately before the formation of the charged droplets and the ease of ejection of the gaseous ions from the charged droplets. The latter factor is related to the size of the charged droplets and the ease of vaporization of the solvent in the droplets. The ejection of the gaseous ions becomes easier as the viscosity of the eluate becomes lower, the surface tension of the eluate becomes lower, or the boiling point of the solvent in the droplets becomes lower. Accordingly, these factors are considered in determining the combination of the additives.

A measurement example of the analyzing method using the LC-MS in the present embodiment is hereinafter described. In the following case, the compounds to be subjected to the measurement are peptides.

In this measurement example, dimethyl sulfoxide (DMSO) was selected as additive A, and 2-propanol as additive B. DMSO is a polar aprotic solvent. It is a reagent which can produce the effect of gathering charge states. This effect of DMSO results from the fact that the high degree of proton affinity of DMSO causes progressive removal of protons from high charge states in which non-localized protons are present in lysine and arginine at the C-terminus of a trypsin-digested peptide or in the N-terminus of the peptide. On the other hand, 2-propanol has the characteristics as shown in the table below. Although its coefficient of viscosity is higher than that of water or acetonitrile used as the mobile phase, it has a lower surface tension, which helps the formation of fine droplets in the spraying process. Its low boiling point also allows for easy vaporization.

TABLE 1

| Solvent | Coefficient of viscosity (cP) | Surface tension (N/m) | Boiling point (° C.) |
| --- | --- | --- | --- |
| water | 1.00 | 0.073 | 100 |
| acetonitrile | 0.37 | 0.029 | 82 |
| 2-propanol | 2.39 | 0.021 | 82 |
| dimethyl sulfoxide (DMSO) | 2.24 | 0.043 | 189 |

The relationship between the flow rates of the two additives and the detection sensitivity was investigated by experiments as follows:

[Experiment 1]

The measurement conditions were as follows:

Compounds subjected to the measurement: two kinds of peptides of tau proteins, 68-STPTAEDVTAPLVDE-GAPGK-87 (molecular ion: $[M+2H]^{2+}$, molecular weight: 978.5540) and 282-LDLSNVQSK-290 (molecular ion: $[M+2H]^{2+}$, molecular weight: 502.5643)

Flow velocity of mobile phase: 100 µL/min (binary gradient)

Mobile phase a: 0.1% formic acid (FA)

Mobile phase b: 0.1% formic acid/acetonitrile

Additive A: 10% dimethyl sulfoxide (DMSO; flow rate: 0-100 µL/min)

Additive B: 2-propanol (flow rate: fixed at 0 µL/min, i.e. not added)

Mode of mass spectrometry: MRM measurement (peptide 68-87: m/z 978.5540>884.4628; peptide 282-290: m/z 502.5643>229.2538)

Figure 2:
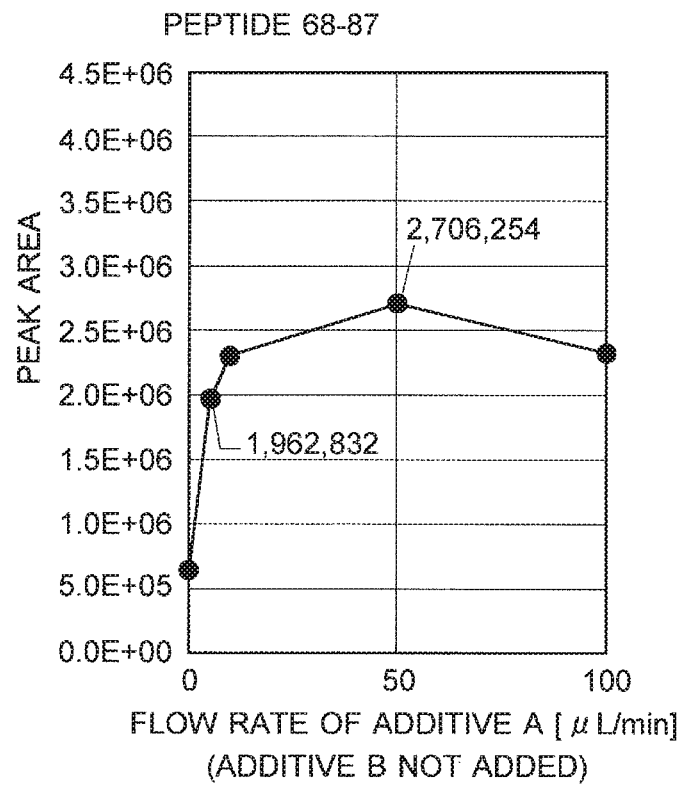
FIG. 2 is a graph showing the result of a measurement of a peak area value for peptides 68-87 with a changing flow rate of additive A (DMSO).
Figure 3:
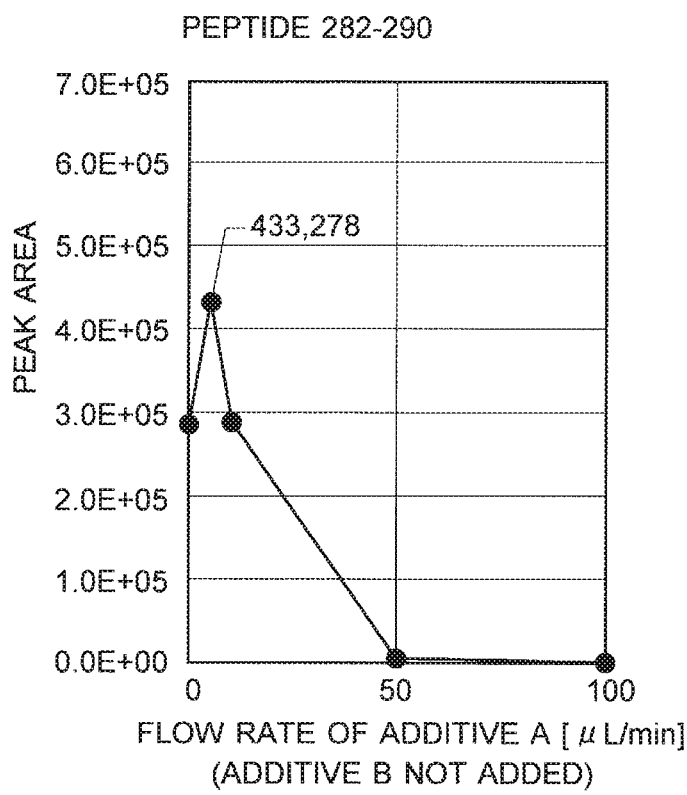
FIG. 3 is a graph showing the result of a measurement of a peak area value for peptides 282-290 with a changing flow rate of additive A (DMSO).

FIG. 2 is the result of the measurement of the relationship between the flow rate of additive A and the peak area value on the mass chromatogram for peptide 68-87. FIG. 3 is the result of the measurement of the relationship between the flow rate of additive A and the peak-area value on the mass chromatogram for peptide 282-290. In the case of peptide 68-87, as shown in FIG. 2, the highest sensitivity (approximately $2.71 \times 10^6$) was obtained when the flow rate of additive A (10% DMSO) was 50 µL/min (the final concentration of DMSO was 3%). It can also be seen that the sensitivity did not increase with the further increase in the flow rate of additive A. In the case of peptide 282-290, the highest level of sensitivity (approximately $4.3 \times 10^5$) was obtained at a lower flow rate of additive A, i.e. 5 µL/min (the final concentration of DMSO was 0.5%). In the latter case, the sensitivity noticeably decreased with the further increase in the flow rate of additive A. The detection was almost impossible when the flow rate was equal to or higher than 50 µL/min.

It seems that such a difference in the relationship between the flow rate of additive A and the peak area depending on the kind of peptide occurs due to the length of the amino acid sequence of the peptide, hydrophobicity of the peptide, contained amount of the acidic amino acid, and other factors.

[Experiment 2]

The measurement conditions were as follows:

Compounds subjected to the measurement: the same as in Experiment 1

Flow velocity of mobile phase: 100 µL/min (binary gradient)

Mobile phase a: 0.1% formic acid (FA)

Mobile phase b: 0.1% formic acid/acetonitrile

Additive A: 10% dimethyl sulfoxide (flow rate: fixed at 5 µL/min)

Additive B: 2-propanol (flow rate: 0-200 µL/min)

Mode of mass spectrometry: the same as in Experiment 1.

Figure 4:
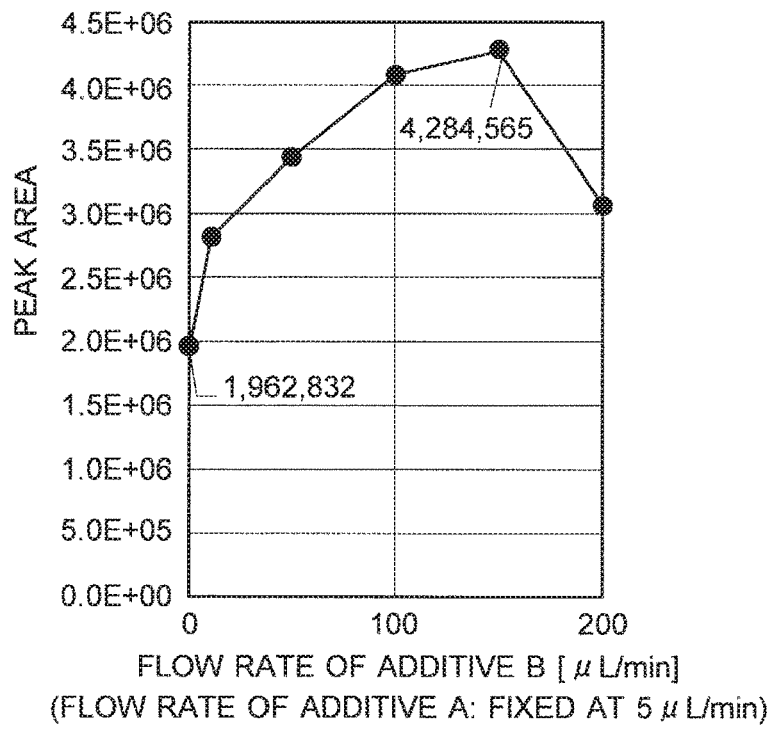
FIG. 4 is a graph showing the result of a measurement of a peak area value for peptides 68-87 with a changing flow rate of additive B (2-propanol) and a fixed flow rate of additive A (DMSO).
Figure 5:
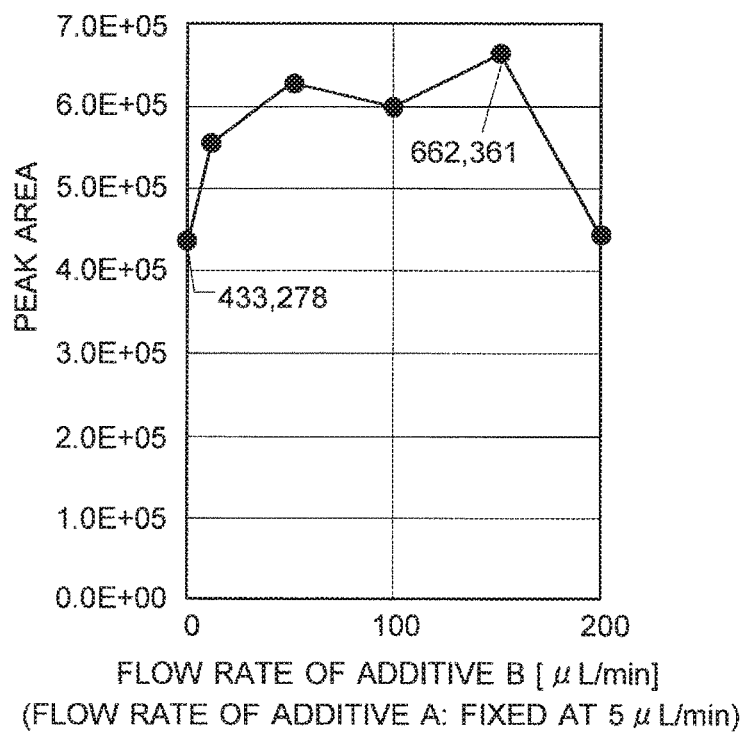
FIG. 5 is a graph showing the result of a measurement of a peak area value for peptides 282-290 with a changing flow rate of additive B (2-propanol) and a fixed flow rate of additive A (DMSO).

FIG. 4 is the result of the measurement of the relationship between the flow rate of additive B and the peak area value on the mass chromatogram for peptide 68-87. FIG. 5 is the result of the measurement of the relationship between the flow rate of additive B and the peak area value on the mass chromatogram for peptide 282-290. As shown in FIGS. 4 and 5, for both peptides, the highest sensitivity (approximately $4.28 \times 10^6$ and $6.6 \times 10^5$) was obtained when the flow rate of additive B (2-propanol) was 150 µL/min. The highest sensitivity increased to a level equal to or even higher than 1.5 times the level achieved in Experiment 1 in which additive B was not added. This result demonstrates that the combined use of additives A and B is effective for improving the detection sensitivity.

From the results of those experiments, it is possible to conclude that a nearly highest detection sensitivity can be obtained for peptide 68-87 and peptide 282-290 by supplying additive A (10% DMSO) at a flow rate of 5 µL/min and additive B (2-propanol) at a flow rate of 150 µL/min. In practice, it is possible that more appropriate conditions may be found by investigating the peak area with a changing flow rate of additive A.

If the target compounds to be detected are previously determined as in the experiments, it is possible to previously and experimentally investigate the combination of the flow rates of two additives A and B which yields the highest detection sensitivity for each target compound. Combinations of the kinds of additives which yield even higher levels of detection sensitivity can also be investigated beforehand. After the flow rates of the additives have been determined for each target compound based on the results of such experiments, the flow-rate program can be created so that the flow rates will be set at appropriate levels at the timing of the elution of each target compound, i.e. at the retention time for each target compound. With the created flow-rate program set as one of the analysis conditions, an LC/MS analysis is performed, whereby signals can be obtained with a nearly highest level of detection sensitivity for each target component.

In the previous embodiment, two additives are mixed in the eluate. It is possible to add one or more additive containers as well as additive supply pumps to mix a total of three or more additives in the eluate.

The combination of the additives is not limited to the one used in the previously described experiments. For example, in an analysis using an acidic mobile phase, a basic additive may be used in combination with an additive for promoting the atomization or vaporization of the droplets (e.g. 2-propanol). This combination improves the detection performance for basic components while achieving an improvement in the overall detection sensitivity. Various other additives already mentioned as examples may also be used.

Furthermore, the previous embodiment is a mere example of the present invention, and any change, modification, addition or the like appropriately made within the spirit of the present invention will naturally fall within the scope of claims of the present application.

REFERENCE SIGNS LIST

1 . . . Liquid Chromatograph Unit (LC Unit)
10a, 10b . . . Mobile Phase Container
11a, 11b . . . Liquid Supply Pump
12 . . . Mixer
13 . . . Injector
14 . . . Column Oven
15 . . . Column
16 . . . Post-Column Adding Unit
161, 162 . . . T-Joint
163A, 163B . . . Additive Container
164A, 164B . . . Additive Supply Pump
17 . . . Eluate Passage
2 . . . Mass Spectrometer Unit (MS Unit)
20 . . . Chamber
2 . . . Mass Spectrometer
201 . . . Ionization Chamber
202 . . . First Intermediate Vacuum Chamber
203 . . . Second Intermediate Vacuum Chamber
204 . . . High Vacuum Chamber
21 . . . ESI Spray
22 . . . Desolvation Tube
23, 25 . . . Ion Guide
24 . . . Skimmer
26 . . . First Quadrupole Mass Filter
27 . . . Collision Cell
28 . . . Second Quadrupole Mass Filter
29 . . . Detector
3 . . . Control Unit
30 . . . LC Control Section
301 . . . Timing Controller
302 . . . Mobile Phase Supply Controller
303 . . . Additive Supply Controller
304 . . . Temperature Controller
31 . . . MS Control Section
4 . . . Data-Processing Unit
5 . . . Input Unit
6 . . . Display Unit

The invention claimed is:

1. A method for liquid chromatographic mass spectrometry in which a liquid chromatograph mass spectrometer employing a mass spectrometer including an atmospheric pressure ion source is used as a detector for a liquid chromatograph, the method including
mixing at least two kinds of additives as a first additive and a second additive into an eluate flowing in a passage connecting an outlet of a column of the liquid chromatograph and the atmospheric pressure ion source, where each of the two additives is mixed into the eluate at an arbitrary flow rate; wherein
the first additive is a reagent which affects a charge state of the eluate; and
the second additive is a reagent which affects a size of droplets of the eluate or vaporization efficiency of the droplets when the eluate is sprayed into an ambience of atmospheric pressure in the atmospheric pressure ion source.

2. The method for liquid chromatographic mass spectrometry according to claim 1, wherein:
the first additive is a reagent for pH control and/or having proton affinity; and
the second additive is a reagent having at least one nature selected from a lower boiling point, a lower surface tension and a lower viscosity than a mobile phase.

3. The method for liquid chromatographic mass spectrometry according to claim 2, wherein:
a sample to be subjected to a measurement is a mixture of a peptide and a glycopeptide; and
the first additive is a pH-control reagent, and the flow rate of the first additive is changed with a passage of time in such a manner that the eluate exiting from the outlet of the column of the liquid chromatograph becomes acidic during a period of time in which the peptide is contained in the eluate, whereas the eluate exiting from the outlet of the column of the liquid chromatograph becomes basic during a period of time in which the glycopeptide is contained in the eluate.

4. The method for liquid chromatographic mass spectrometry according to claim 1, wherein:
the first additive is dimethyl sulfoxide, and the second additive is 2-propanol.

5. The method for liquid chromatographic mass spectrometry according to claim 2, wherein:
the first additive is dimethyl sulfoxide, and the second additive is 2-propanol.

6. The method for liquid chromatographic mass spectrometry according to claim 1, wherein:
the atmospheric pressure ion source is an electrospray ion source.

7. A liquid chromatograph mass spectrometer in which a mass spectrometer provided with an atmospheric pressure ion source is used as a detector for a liquid chromatograph, comprising:
a) an additive supplier for mixing an additive into an eluate flowing in a passage connecting an outlet of a column of the liquid chromatograph and the atmospheric pressure ion source, the additive supplier comprising at least a first additive supply section for mixing a first additive at a given flow rate into the eluate and a second additive supply section for mixing a second additive at a given flow rate into the eluate; and
b) a controller programmed to control the flow rate of the first additive supplied by the first additive supply section and the flow rate of the second additive supplied by the second additive supply section, the flow rates adjusted independently of each other.

8. The liquid chromatograph mass spectrometer according to claim 7, wherein:
the controller changes the flow rate of the first additive and the flow rate of the second additive individually according to a passage of time.

* * * * *